US006242179B1

(12) United States Patent
Shah et al.

(10) Patent No.: US 6,242,179 B1
(45) Date of Patent: Jun. 5, 2001

(54) HUMAN PHOSPHATASES

(75) Inventors: Purvi Shah, Sunnyvale; Jennifer L. Hillman; Neil C. Corley, both of Mountain View; Preeti Lal, Santa Clara, all of CA (US)

(73) Assignee: Incyte Pharmaceuticals, Inc., Palo Alto, CA (US)

( * ) Notice: Subject to any disclaimer, the term of this patent is extended or adjusted under 35 U.S.C. 154(b) by 0 days.

(21) Appl. No.: 08/992,035

(22) Filed: Dec. 17, 1997

(51) Int. Cl.$^7$ .............................. C12N 15/55; C12N 9/18; C12N 15/63; C12Q 1/68
(52) U.S. Cl. ....................... 435/6; 536/23.2; 536/23.1; 536/23.5; 435/320.1; 435/252.3; 435/325; 435/196; 435/69.1
(58) Field of Search .................................. 536/23.2, 23.1, 536/23.5; 435/320.1, 252.3, 325, 196, 69.1, 6

(56) References Cited

FOREIGN PATENT DOCUMENTS

WO 98/46730  10/1998  (WO) .

OTHER PUBLICATIONS

A.R. Rodaway et al., "Characterization of the 47–Kilodalton Autosomal Chronic Granulomatous Disease Protein: Tissue–Specific Expression and Transcriptional Control By Retinoic Acid" Mol. Cell. Biol. 10(10):5388–5396, Oct. 1990.
GenBank entry H97570, Dec. 1995.
GenBank entry N25122, Dec. 1995.
GenBank entry AA043085, Sep. 1996.
Kai KM, et al.: "Cloning and characterization of two human isozymes of Mg2+independent phosphatidic acid phosphatases" Journal of Biological Chemistry, vol. 272, No. 39, Sep. 26, 1997 (Sep. 26, 1997), pp. 24572–24578, XP002101936.
Leung D.W. et al.: "Molecular cloning of two alternatively spliced forms of human phosphatidic acid phosphatase cDNA that are differently expressed in normal tumor cells" DNA Cell Biology, vol. 17, No. 4, Apr. 1998 ( Apr. 1998), pp. 377–385, XP002101937.
Charbonneau, H. and Tonks, N.K., "1002 protein Phosphatases?," *Ann. Rev. Cell. Biol.*, 8:463–93 (.1992)
Day, C.P, et al., "Plasma membrane form of phosphatidate phosphohydrolase: a possible role in signal transduction during liver Fibrogenesis," *Clinical Science*, 85:281–287 (1993).
Kai, M., et al., (GI 1487873), GenBank Sequence Database (Accession D84376), National Center for Biotechnology Information, National Library of Medicine, Bethesda, Maryland 20894 (Oct. 1996).
Kai, M., et al., (GI 1487872), GenBank Sequence Database (Accession D84376), National Center for Biotechnology Information, National Library of Medicine, Bethesda, Maryland 20894 (Oct. 1996).
Kondo, H., et al., (GI 2285789), GenBank Sequence Database (Accession AB002086), National Center for Biotechnology Information, National Library of Medicine, Bethesda, Maryland 20894 (Jul. 1997).
Kai, M., et al., "Identification and cDNA Cloning of 35–kda Phosphatidic Acid Phosphatase (Type 2) Bound to Plasma Membranes," *The Journal of Biological Chemistry*, 271(31) :18931–18938 (1996) (GI 1487872 and 1487873).
Kondo, H., et al., "p47 is a cofactor for p97–mediated membrane fusion," *Nature*, 388:75–79 (1997) (GI 2285789 and 2285790).
Waite, K., et al., "Phosphatidic Acid–mediated Phosphorylation of the NADPH Oxidase Component p47–phox," *The Journal of Biological Chemistry*,272(24) :15569–15578 (1997).

Primary Examiner—Rebecca E. Prouty
(74) *Attorney, Agent, or Firm*—Incyte Pharmaceuticals, Inc.

(57) ABSTRACT

The invention provides human phosphatases (HPA) and polynucleotides which identify and encode HPA. The invention also provides expression vectors, host cells, antibodies, agonists, and antagonists. The invention also provides methods for treating disorders associated with expression of HPA.

10 Claims, 17 Drawing Sheets

```
                9              18           27          36          45          54
NNT CGC CAG CCC CGG GGG CTC GAG AAT CAA GGG CCT CGG CCG TCC CGC 63             72           81          90          99          108
AGC TCA GTC CAT CGC CCT TGC CGG GCA GCC CGG GAG ACC ATG TTT GAC AAG
                                                       M   F   D   K 117            126          135         144         153         162
ACG CGG CTG CCG TAC GTG GCC CTC GAT GTG CTC TGC GTG TTG CTG GCT TCC ATG
 T   R   L   P   Y   V   A   L   D   V   L   C   V   L   L   A   S   M 171            180          189         198         207         216
CCT ATG GCT GTT CTA AAA TTG GGC CAA ATA TAT CCA TTT CAG AGA GGC TTT TTC
 P   M   A   V   L   K   L   G   Q   I   Y   P   F   Q   R   G   F   F 225            234          243         252         261         270
TGT AAA GAC AAC AGC ATC AAC TAT CCG TAC CAT GAC AGT ACC GTC ACA TCC ACT
 C   K   D   N   S   I   N   Y   P   Y   H   D   S   T   V   T   S   T 279            288          297         306         315         324
GTC CTC ATC CTA GTG GGG GTT GGC TTG CCC ATT TCC TCT ATT CTT GGA GAA
 V   L   I   L   V   G   V   G   L   P   I   S   S   I   L   G   E 333            342          351         360         369         378
ACC CTG TCT GTT TAC TGT AAC CTT TTG CAC TCA AAT TCC TTT ATC AGG AAT AAC
 T   L   S   V   Y   C   N   L   L   H   S   N   S   F   I   R   N   N
```

FIGURE 1A

```
                387         396         405         414         423         432
TAC ATA GCC ACT ATT TAC AAA GCC ATT GGA ACC TTT TTA TTT GGT GCA GCT GCT
 Y   I   A   T   I   Y   K   A   I   G   T   F   L   F   G   A   A   A 441         450         459         468         477         486
AGT CAG TCC CTG ACT GAC ATT GCC AAG TAT TCA ATA GGC AGA CTG CGG CCT CAC
 S   Q   S   L   T   D   I   A   K   Y   S   I   G   R   L   R   P   H 495         504         513         522         531         540
TTC TTG GAT GTT TGT GAT CCA GAT TGG TCA AAA ATC AAC TGC AGC GAT GGT TAC
 F   L   D   V   C   D   P   D   W   S   K   I   N   C   S   D   G   Y 549         558         567         576         585         594
ATT GAA TAC TAC ATA TGT CGA GGG AAT GCA GAA AGA GTT AAG GAA GGC AGG TTG
 I   E   Y   Y   I   C   R   G   N   A   E   R   V   K   E   G   R   L 603         612         621         630         639         648
TCC TTC TAT TCA GGC CAC TCT TCG TTT TCC ATG TAC TGC ATG CTG TTT GTG GCA
 S   F   Y   S   G   H   S   S   F   S   M   Y   C   M   L   F   V   A 657         666         675         684         693         702
CTT TAT CTT CAA GCC AGG ATG AAG GGA GAC TGG GCA AGA CTC TTA CGC CCC ACA
 L   Y   L   Q   A   R   M   K   G   D   W   A   R   L   L   R   P   T
```

FIGURE 1B

```
      711          720       729       738       747       756
CTG CAA TTT GGT CTT GTT GCC GTA TCC ATT TAT GTG GGC CTT TCT CGA GTT TCT
 L   Q   F   G   L   V   A   V   S   I   Y   V   G   L   S   R   V   S 765          774       783       792       801       810
GAT TAT AAA CAC CAC TGG AGC GAT GTG TTG ACT GTG TTG ACT GGA CTC ATT CAG GGA GCT CTG
 D   Y   K   H   H   W   S   D   V   L   T   G   L   I   Q   G   A   L 819          828       837       846       855       864
GTT GCA ATA TTA GTT GCT GTA TAT GTA TCG GAT TTC TTC AAA GAA AGA ACT TCT
 V   A   I   L   V   A   V   Y   V   S   D   F   F   K   E   R   T   S 873          882       891       900       909       918
TTT AAA GAA AGA AAA GAG GAG GAC TCT CAT ACA ACT CTG CAT ACA ACA CCA ACA
 F   K   E   R   K   E   E   D   S   H   T   T   L   H   E   T   P   T 927          936       945       954       963       972
ACT GGG AAT CAC TAT CCG AGC AAT CAC CAG CCT TGA AAG GCA GCA GGG TGC CCA
 T   G   N   H   Y   P   S   N   H   Q   P 981          990       999       1008      1017      1026
GGT GAA GCT GGC CTG TTT TCT AAA GGA AAA TGA TTG CCA CAA GGC AAG AGG ATG 1035         1044      1053      1062      1071      1080
CAT CTT TCT TCC TGG TGT ACA AGC CTT TAA AGA CTT CTG CTA TGC CTC
```

FIGURE 1C

```
      1089           1098           1107         1116           1125         1134
TTG GAT GCA CAC TTT GTG TGT ACA TAG TTA CCT TTA ACT CAG TGG TTA TCT AAT 1143           1152           1161         1170           1179         1188
AGC TCT AAA CTC ATT AAA AAA ACT CCA AGC CTT CCA CCA AAA CAG TGC CCC ACC 1197           1206           1215         1224           1233         1242
TGT ATA CAT TTT TAT TAA AAA AAT GTA ATG CTT ATG TAT AAA CAT GTA TGT AAT 1251           1260           1269         1278           1287         1296
ATG CTT TCT ATG AAT GAT GTT TGA TTT AAA TAT AAT ACA TAT TAA AAT GTA TGG 1305           1314
GAG AAC CAA AAA AAA AAA A 3'
```

```
5' AAG ATG GCG GCG GAG CGA CAG GAG GCG CTG AGG GAG TTC GTG GCG GTG ACG GGC
     M   A   A   E   R   Q   E   A   L   R   E   F   V   A   V   T   G

GCC GAG GAC CGG CGC TTC CTC TTT TAT GAG GGA GGG GAT GAA GAC TGG GAC TTG CAG
    A   E   D   R   R   F   L   F   Y   E   G   G   D   E   D   W   D   L   Q

ATC GCG CTA GCG AGC TTT TAT GAG GAC CTC ATT GAC CAT CAG AGT GGA AGT GAC CTG AGA
    I   A   L   A   S   F   Y   E   D   L   I   D   H   Q   S   G   S   D   L   R

TCG CAG GCA ACC CCC AGT TCA GTG TCC AGA GGC TCA GAG AGA AGT GGA GAG GAG GAA GAG
    S   Q   A   T   P   S   S   V   S   R   G   S   E   R   S   G   E   E   E   E

GTG ACA TCC TTC AGA GAC CTC ATT CAT GAC CAA GAG AGT GGA GAT GAG GAG GAG GAG
    V   T   S   F   R   D   L   I   H   D   Q   E   S   G   D   E   E   E   E

GAA GGC CAG AGG TTT TAT GCT GGG TCA GAG AGA AGT GGA GAG GAG GAG GAG GAG

GGC CCT CCC AGG AAG AGT CCC AAC GAG CTG GTG GAT GAT CTC TTT AAA GGT
    G   P   P   R   K   S   P   N   E   L   V   D   D   L   F   K   G
```

FIGURE 4A

```
        387             396     405     414     423     432
GCC AAA GAG CAT GGA GCT GTA GCT GAG CGA GTG ACC AAG AGC CCT GGA GAG
 A   K   E   H   G   A   V   A   E   R   V   T   K   S   P   G   E 441             450     459     468     477     486
ACC AGT AAA CCG AGA CCA TTT GCA GGA GGT GGC TAC CGC CTT GGG GCA GCA CCA
 T   S   K   P   R   P   F   A   G   G   G   Y   R   L   G   A   A   P 495             504     513     522     531     540
GAG GAA TCT GCC TAT GTG GCA GGA GAA AAG AGG CAG CAT TCC AGC CAA GAT
 E   E   S   A   Y   V   A   G   E   K   R   Q   H   S   S   Q   D 549             558     567     576     585     594
GTT CAT GTA GTA TTG AAA CTC TGG AAG AGT GGA TTC AGC CTG GAT AAT GGA GAA
 V   H   V   V   L   K   L   W   K   S   G   F   S   L   D   N   G   E 603             612     621     630     639     648
CTC AGA AGC TAC CAA GAC CCA TCC AAT GCC CAG TTT CTG GAG TCT ATC CGC AGA
 L   R   S   Y   Q   D   P   S   N   A   Q   F   L   E   S   I   R   R 657             666     675     684     693     702
GGG GAG GTG CCA GCA GAG CTT CGG AGG CTA GCT CAC GGT GGA CAG GTG AAC TTG
 G   E   V   P   A   E   L   R   R   L   A   H   G   G   Q   V   N   L
```

FIGURE 4B

```
              711        720        729        738        747        756
GAT ATG GAG GAC CAT CGG GAC GAG TTT GTG AAG CCC AAA GGA GCC TTC AAA
 D   M   E   D   H   R   D   E   F   V   K   P   K   G   A   F   K 765        774        783        792        801        810
GCC TTC ACT GGC GAG GGT CAG AAA CTG GGC AGC ACT GCC CCC CAG GTG TTG AGT
 A   F   T   G   E   G   Q   K   L   G   S   T   A   P   Q   V   L   S 819        828        837        846        855        864
ACC AGC TCT CCA GCC CAA CAG GCA GAA AAT GAA AAA GCC AGC TCT TCC ATC
 T   S   S   P   A   Q   Q   A   E   N   E   K   A   S   S   S   I 873        882        891        900        909        918
TTA ATC GAC GAA TCA GAG CCT ACC ACA AAC ATC CAA ATT CGG CTT GCA GAC GGC
 L   I   D   E   S   E   P   T   T   N   I   Q   I   R   L   A   D   G 927        936        945        954        963        972
GGG AGG CTG GTG CAG AAA TTT AAC CAC AGC AGG ATC AGC GAC ATC CGA CTC
 G   R   L   V   Q   K   F   N   H   S   R   I   S   D   I   R   L 981        990        999        1008       1017       1026
TTC ATC GTG GAT GCC CGG CCA GCC ATG GCT GCC ACC AGC TTT ATC CTC ATG ACT
 F   I   V   D   A   R   P   A   M   A   A   T   S   F   I   L   M   T
```

FIGURE 4C

```
              1035                1044            1053            1062            1071            1080
ACT TTC CCG AAC AAA GAG CTG GCT GAT GAG AGC CAG ACC CTG AAG GAA GCC AAC
 T   F   P   N   K   E   L   A   D   E   S   Q   T   L   K   E   A   N 1089                1098            1107            1116            1125            1134
CTG CTC AAT GCT GTC ATC GTG CAG CGG TTA ACA TAA CCG CCC AGC CAG CTG CCT
 L   L   N   A   V   I   V   Q   R   L   T   *

1143                1152            1161            1170            1179            1188
GGC CTC CCT CCT GTG TTT CCC ATG GCC AGT GGC CAT GCC CCA TGG GGA TCG CCC 1197                1206            1215            1224            1233            1242
CTC CTG CCC CCT TGT GCA CAC CCA GTC CAG TGC AAC GTC TCC TCC ATA GCT 1251                1260            1269            1278            1287            1296
CTG GGT TCT TAG ATC TTG GTT GGA CGT TTG TTT TCT CCT TAG TTG CAT TTC CTG 1305                1314            1323            1332            1341            1350
GGT TTT TGT GAT GAT CAA TGG ACT TTA ATG AAA AAA ATA AAA ACA ACC AAA 1359                1368            1377            1386            1395            1404
AAA ATT GAA GGA ATA TCA CCA GCA TGT TGT ACG GAA ACT CTC CCA CTG AAG CAG 1413                1422            1431            1440            1449            1458
GCT TTA ATT GCT TTA AAA TTA TAT TTA TCT TGG GGC CTG TGG GAG GAA TCT TCC
```

FIGURE 4D

```
      1467        1476        1485        1494        1503        1512
TTC CAT CTT CTC TGC ATA AAA ACT TGT GGC ACA CAA TGC TTA TTC ACT AGT GTG
      1521        1530        1539        1548        1557        1566
TCC CAC CCG CCA GCC CCA CAG ATG ACT GGA AGG AGG GGA AAT GTG TAG AAA
      1575        1584        1593        1602        1611        1620
GAG GCT TCG CCA CCA CTT GTT CCC ACG AGA ATA TAT CAC TTG CCC AGA TAA AAC
      1629        1638        1647        1656        1665        1674
TGG GCG GCA GCA GAG TTC CCT GAA GTG GGA AGT CAG AGC TCC ATG CAC ACA GTG
      1683        1692        1701        1710        1719        1728
TCT TCA GAA GGT GAA AAT AAA TAT TTC CCT GTG CTC CTT TTA CTC AAC CCC TGG
      1737        1746        1755        1764        1773        1782
GGT ATC TAA TCT TGC CAG GTC TTG GCC AGT TGA GAT TCT GTT CCA CCT GCC TGC
      1791        1800        1809        1818        1827        1836
CTG GCC CTT TCC TCC ATT ACC ATC CAG ACT GCT CGC CTC CTG GGG ATT CTC AGG
      1845        1854        1863        1872        1881        1890
GGC TCC ATT ATG GCT TGA TTT ACT CCA CGT GCA GAA GTC TTG AGT GGA CCT AGG
```

FIGURE 4E

```
          1899            1908            1917            1926            1935            1944
AGG TAG GTG GGA TAT TTT TCA CTA GGA TAC AGC TCA TGC CAA CCC ATC CTA 1953            1962            1971            1980            1989            1998
AGT GAG TTC AGA ATC AGG GTA TCT TGC CCT AAA AGA TAA ACA GTC AAA ATG CCA 2007            2016            2025            2034            2043            2052
CCG AGC TGT TCA CTA GTG ATG TGT GGC AAA TCA AAT CAA CTG TTG AAG AAG GGG 2061            2070            2079            2088            2097            2106
TGA GTT TTC TGT GCT ACA AGC ACC TGT CAC TGT TGG TAC TTG CAG GAG GCT TCT 2115            2124            2133            2142            2151            2160
GCT GGG TAT GTT TTG GAA GTG AGT GTC ACT ACT TGG CTT TGC TTA GCA GGT TCT 2169            2178            2187            2196            2205            2214
GCT TCA CAC TTG TTC TTT GAC CTG CTG ACT TGT GAC TTG CAG AAA CAT AGG CAG 2223            2232            2241            2250            2259            2268
TAG TCC TAG CCT GGT AAA GAC CCT CCA CCA CCC CTA TAA GTT TGA TTG CTA TGC 2277            2286            2295            2304            2313            2322
AGG TTT GGG AGA GGA GGC CTA TTG GGC TCT TGG ATG GAA CCC TTT CCC GTA TTA 2331            2340            2349            2358            2367            2376
AAC AAA CCA GAG ACA GAA TCA GTG CTG ACT CAG GAT CTC CTG GTT TGG AAT CGT
```

FIGURE 4F

```
       2385            2394            2403            2412            2421            2430
AAT GTG CCT CAA TCC TCT TTC CAA GCA GGC CTC ACC AGT CTC TTT CTC TTT CCT
       2439            2448            2457            2466            2475            2484
GCT TCA CCC CTG CAA TGA GCC AAG AAC CAA CAC TAC ATC CAC CTA GAA CTG CAG
       2493            2502            2511            2520            2529            2538
AAG GGC TTG TGG TTT CAA CCA AGA CCC ATC CTG AGC AAG GGA CTT GGC TTG GTG
       2547            2556            2565            2574            2583            2592
CTT TTG ATC CCA AAG TTC CCA CAC CGG CAG TGG CCT GCT GGG GCA ATG GCA TCT
       2601            2610            2619            2628            2637            2646
GTC ACG GTG TTT TCT CCA GCA GGT GGA GAT TAT GGA ACC TAC ATA TGG GTC TGG
       2655            2664            2673            2682            2691            2700
AAA AAC TGT ACA CTG TTG TCA CCT TGA CCA TTA AAA ACC AGA ATG AGG ACA AAA

AAA AAC A 3'
```

HUMAN PHOSPHATASES

FIELD OF THE INVENTION

This invention relates to nucleic acid and amino acid sequences of human phosphatases and to the use of these sequences in the diagnosis, prevention, and treatment of immune disorders and diseases associated with cancer.

BACKGROUND OF THE INVENTION

The protein phosphorylation/dephosphorylation cycle is one of the major regulatory mechanisms employed by eukaryotic cells to control cellular activities. It is estimated that more than 10% of the active proteins in a typical mammalian cell are phosphorylated. During protein phosphorylation/dephosphorylation, phosphate groups are transferred from adenosine triphosphate molecules to a protein by protein kinases and are removed from a protein by protein phosphatases.

Protein phosphatases function in cellular signaling events that regulate cell proliferation and differentiation, cell-to-cell contacts, the cell cycle, and oncogenesis. Three evolutionary distinct protein phosphatase families have been identified. These include the serine/threonine phosphatases, the protein tyrosine phosphatases, and the acid/alkaline phosphatases (Carbonneau H. and Tonks N. K. (1992) Annu. Rev. Cell Biol. 8:463–93).

Phosphatidic acid phosphate (PAP) is metabolized to diacylglycerol in the classical pathway of glycerolipid biosynthesis by dephosphorylating phosphatidic acid. Phosphatidic acid and its metabolic derivative, lysophosphatidic acid, are known to be potent mitogens and activators when exogenously added to different cells. Two isoforms of PAP exist in rat liver. The first, designated PAP1, is associated with the cytosol and microsomes, and appears to be responsible for glycerolipid biosynthesis. The second isoform PAP2 is bound to the plasma membrane and is involved in cellular signal transduction. The activities of the two PAP isoforms appear to undergo different activity alterations in several liver diseases (Day, C. P (1993) Clin. Sci. (Lond.) 85:281–287).

Phospholipase D (PLD) is activated in a variety of cells by hormones and growth factors. Activated PLD results in the generation of phosphatidic acid (PA) by hydrolysis of PAP, which can be further metabolized by PA phosphohydrolase to diacylglycerol (DG). The generation of PA by PLD in neutrofils has been linked to the activation of the respiratory burst enzyme, NADPH oxidase. During phosphorylation-dependent oxidase activation, PA, but not DG, induces phosphorylation of a wide range of proteins, the most prominent of which is the NADPH oxidase component p47-phox (phagocytic oxidase component). The absence of p47-phox is implicated in a genetic defect called p47-phox-deficient chronic granulomatous disease (P47-GCD). P-47-GCD is caused by a GT deletion at the beginning of exon 2. The GT deletion has been found in 11 becteriophage and 15 YAC clones.

The discovery of two new human protein phosphatases and the polynucleotides encoding them satisfies a need in the art by providing new compositions which are useful in the diagnosis, prevention and treatment of immune disorders and diseases associated with cancer.

SUMMARY OF THE INVENTION

The invention features substantially purified polypeptides, human phosphatases, referred to collectively as "HPA" and individually as "HPA-1" and "HPA-2." In one aspect, the invention provides a substantially purified polypeptide, HPA, comprising an amino acid sequence selected from the group consisting of SEQ ID NO:1, SEQ ID NO:4, a fragment of SEQ ID NO:1, and a fragment of SEQ ID NO:4.

The invention further provides a substantially purified variant of HPA having at least 90% amino acid identity to the amino acid sequences of SEQ ID NO:1 or SEQ ID NO:4, or to a fragment of either of these sequences. The invention also provides an isolated and purified polynucleotide sequence encoding the polypeptide comprising any of the amino acid sequences described above. The invention also includes an isolated and purified polynucleotide variant having at least 90% polynucleotide identity to the polynucleotide sequence encoding the polypeptide comprising these amino acid sequences.

Additionally, the invention provides a composition comprising a polynucleotide sequence encoding the polypeptide comprising the amino acid sequence of SEQ ID NO:1, SEQ ID NO:4, a fragment of SEQ ID NO:1, or a fragment of SEQ ID NO:4. The invention further provides an isolated and purified polynucleotide sequence which hybridizes under stringent conditions to one of these polynucleotide sequences, as well as an isolated and purified polynucleotide sequence which is complementary to one of these polynucleotide sequences.

The invention also provides an isolated and purified polynucleotide sequence comprising a polynucleotide sequence selected from the group consisting of SEQ ID NO:2, SEQ ID NO:5, a fragment of SEQ ID NO:2, and a fragment of SEQ ID NO:5. The invention further provides an isolated and purified polynucleotide variant having at least 90% polynucleotide identity to one of these polynucleotide sequences, as well as an isolated and purified polynucleotide sequence which is complementary to one of these polynucleotide sequences.

The invention further provides an expression vector containing at least a fragment of any of the claimed polynucleotide sequences. In another aspect, the expression vector containing the polynucleotide sequence is contained within a host cell.

The invention also provides a method for producing a polypeptide comprising the amino acid sequence of SEQ ID NO:1, SEQ ID NO:4, a fragment of SEQ ID NO:1, and a fragment of SEQ ID NO:4, the method comprising the steps of: (a) culturing the host cell containing an expression vector containing at least a fragment of a polynucleotide sequence encoding HPA under conditions suitable for the expression of the polypeptide; and (b) recovering the polypeptide from the host cell culture.

The invention also provides a pharmaceutical composition comprising a substantially purified HPA having the amino acid sequence of SEQ ID NO:1, SEQ ID NO:4, a fragment of SEQ ID NO:1, or a fragment of SEQ ID NO:4 in conjunction with a suitable pharmaceutical carrier.

The invention further includes a purified antibody which binds to a polypeptide comprising the amino acid sequence of SEQ ID NO:1, SEQ ID NO:4, a fragment of SEQ ID NO:1, or a fragment of SEQ ID NO:4, as well as a purified agonist and a purified antagonist to the polypeptide.

The invention also provides a method for treating or preventing an immune disorder, the method comprising administering to a subject in need of such treatment an effective amount of an antagonist of HPA.

The invention also provides a method for treating or preventing a cancer, the method comprising administering to a subject in need of such treatment an effective amount of an antagonist of HPA.

The invention also provides a method for detecting a polynucleotide encoding HPA in a biological sample containing nucleic acids, the method comprising the steps of: (a) hybridizing the complement of the polynucleotide sequence which encodes the polypeptide comprising SEQ ID NO:1, SEQ ID NO:4, a fragment of SEQ ID NO:1, or a fragment of SEQ ID NO:4 to at least one of the nucleic acids of the biological sample, thereby forming a hybridization complex; and (b) detecting the hybridization complex, wherein the presence of the hybridization complex correlates with the presence of a polynucleotide encoding HPA in the biological sample. In one aspect, the nucleic acids of the biological sample are amplified by the polymerase chain reaction prior to the hybridizing step.

BRIEF DESCRIPTION OF THE FIGURES.

FIGS. 1A, 1B, 1C, and 1D shows the amino acid sequence (SEQ ID NO:1) and nucleic acid sequence (SEQ ID NO:2) of HPA-1. The alignment was produced using MacDNASIS PRO™ software (Hitachi Software Engineering Co. Ltd. San Bruno, Calif.).

FIG. 2 shows the amino acid sequence alignments between HPA-1(1719418 SEQ ID NO:1) and phosphatidic acid phosphatase (GI 1487873; SEQ ID NO:3), produced using the multisequence alignment program of DNASTAR™ software (DNASTAR Inc, Madison Wis.).

FIGS. 4A, 4B, 4C, 4D, 4E, 4F, and 4G show the amino acid sequence (SEQ ID NO:4) and nucleic acid sequence (SEQ ID NO:5) of HPA-2. The alignment was produced using MacDNASIS PRO™ software (Hitachi Software Engineering Co. Ltd. San Bruno, Calif.).

FIG. 5 shows the amino acid sequence alignments between HPA-2 (1734452; SEQ ID NO:4) and p47 (GI 2285790; SEQ ID NO:6), produced using the multisequence alignment program of DNASTAR™ software (DNASTAR Inc, Madison Wis.).

DESCRIPTION OF THE INVENTION

Figure 3A:
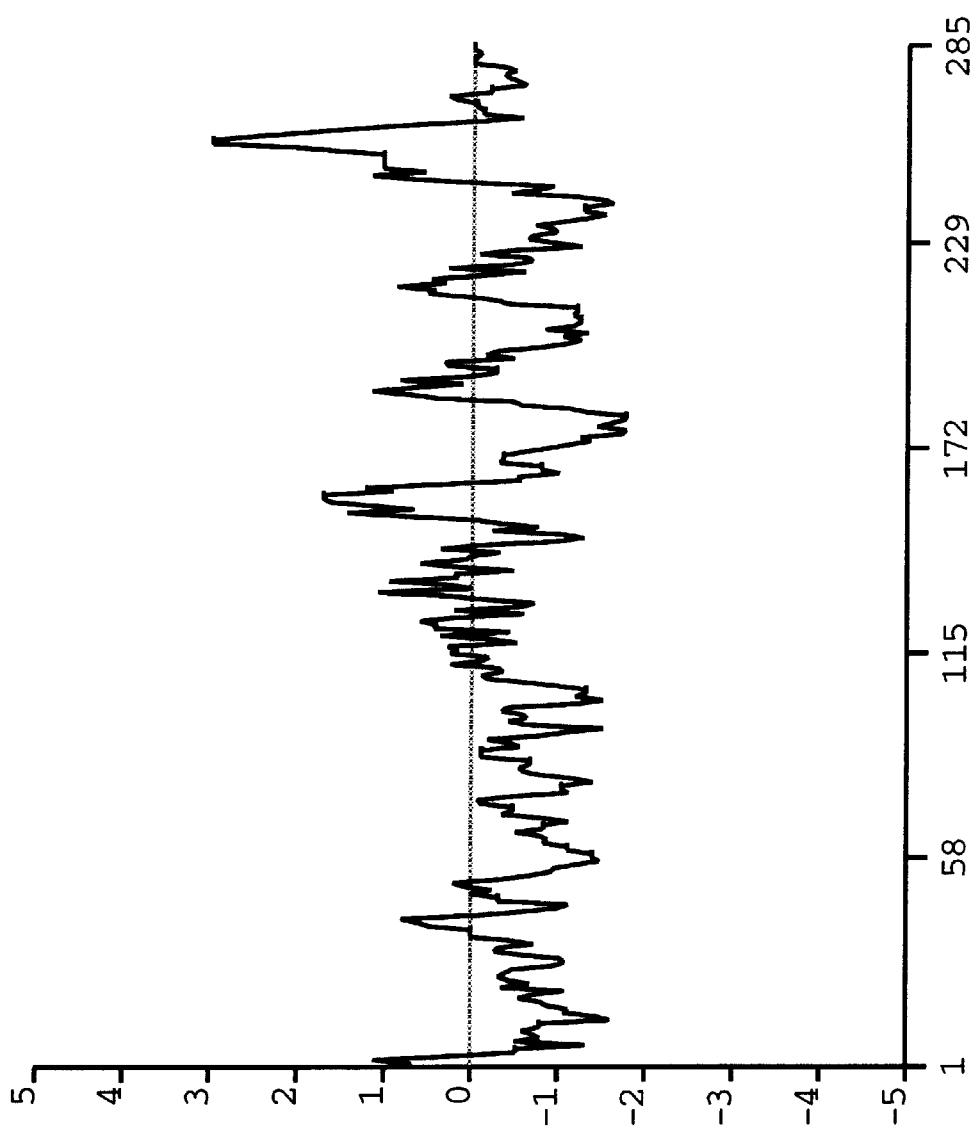
FIGS. 3A and 3B show the hydrophobicity plots for HPA-1, SEQ ID NO:1 and phosphatidic acid phosphatase (SEQ ID NO:3), respectively ; the positive X axis reflects amino acid position, and the negative Y axis, hydrophobicity (MacDNASIS PRO software).

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

HPA, as used herein, refers to the amino acid sequences of substantially purified HPA obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to HPA, increases or prolongs the duration of the effect of HPA. Agonists may include proteins, nucleic acids, carbohydrates, or any other molecules which bind to and modulate the effect of HPA.

An "allele" or "allelic sequence", as used herein, is an alternative form of the gene encoding HPA. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding HPA as used herein include those with deletions, insertions, or substitutions of different nucleotides resulting in a polynucleotide that encodes the same or a functionally equivalent HPA. Included within this definition are polymorphisms which may or may not be readily detectable using a particular oligonucleotide probe of the polynucleotide encoding HPA, and improper or unexpected hybridization to alleles, with a locus other than the normal chromosomal locus for the polynucleotide sequence encoding HPA. The encoded protein may also be "altered" and contain deletions, insertions, or substitutions of amino acid residues which produce a silent change and result in a functionally equivalent HPA. Deliberate amino acid substitutions may be made on the basis of similarity in polarity, charge, solubility, hydrophobicity, hydrophilicity, and/or the amphipathic nature of the residues as long as the biological or immunological activity of HPA is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of HPA are preferably about 5 to about 15 amino acids in length and retain the biological activity or the immunological activity of HPA. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) PCR Primer. a Laboratory Manual, Cold Spring Harbor Press, Plainview, N.Y.).

The term "antagonist" as used herein, refers to a molecule which, when bound to HPA, decreases the amount or the duration of the effect of the biological or immunological activity of HPA. Antagonists may include proteins, nucleic acids, carbohydrates, antibodies or any other molecules which decrease the effect of HPA.

As used herein, the term "antibody" refers to intact molecules as well as fragments thereof, such as Fa, F(ab')$_2$, and Fv, which are capable of binding the epitopic determinant. Antibodies that bind HPA polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic HPA, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence", as used herein, refers broadly to any composition containing the given polynucleotide sequence. The composition may comprise a dry formulation or an aqueous solution. Compositions comprising polynucleotide sequences encoding HPA (SEQ ID NO:1) or fragments thereof (e.g., SEQ ID NO:2 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR™ (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW™ Fragment Assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2 or SEQ ID NO:5 by northern analysis is indicative of the presence of mRNA encoding HPA in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to HPA or the encoded HPA. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear micro-chromosomes which may contain DNA sequences of 10K to 10M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of HPA. For example, modulation may cause an increase or a decrease in protein activity, binding characteristics, or any other biological, functional or immunological properties of HPA.

"Nucleic acid" sequence, as the phrase is used herein, refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "sample", as used herein, is used in its broadest sense. A biological sample suspected of containing nucleic acid encoding HPA, or fragments thereof, or HPA itself may comprise a bodily fluid, extract from a cell, chromosome, organelle, or membrane isolated from a cell, a cell, genomic DNA, RNA, or cDNA (in solution or bound to a solid support, a tissue, a tissue print, and the like.

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

As used herein, the term "stringent conditions" refers to conditions which permit hybridization between polynucleotide sequences and the claimed polynucleotide sequences. Suitably stringent conditions can be defined by, for example, the concentrations of salt and/or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5X SSPE, 0.3% SDS, and 200 μg/ml sheared and denatured salmon sperm DNA. Hybridization could occur under reduced stringency conditions as described above, but in 35% formamide or/and at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of HPA, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

THE INVENTION

The invention is based on the discovery of two new human phosphatases human phosphatases HPA-1 and HPA-2 (hereinafter collectively referred to as "HPA"), the polynucleotides encoding HPA, and the use of these compositions for the diagnosis, prevention, or treatment of immune disorders and diseases associated with cancer.

Nucleic acids encoding the HPA-1 of the present invention were first identified in Incyte Clone 1719418 from the bladder cDNA library (BLADNOT06) using a computer search for amino acid sequence alignments. A consensus sequence, SEQ ID NO:2, was derived from the following overlapping and/or extended nucleic acid sequences: Incyte Clones 1719418 (BLADNOT06), 1985948 (LUNGAST01), 1723937 (PROSNOT14), 031187 (THP1NOB01), and 117776 (KIDNNOT01).

Figure 3B:
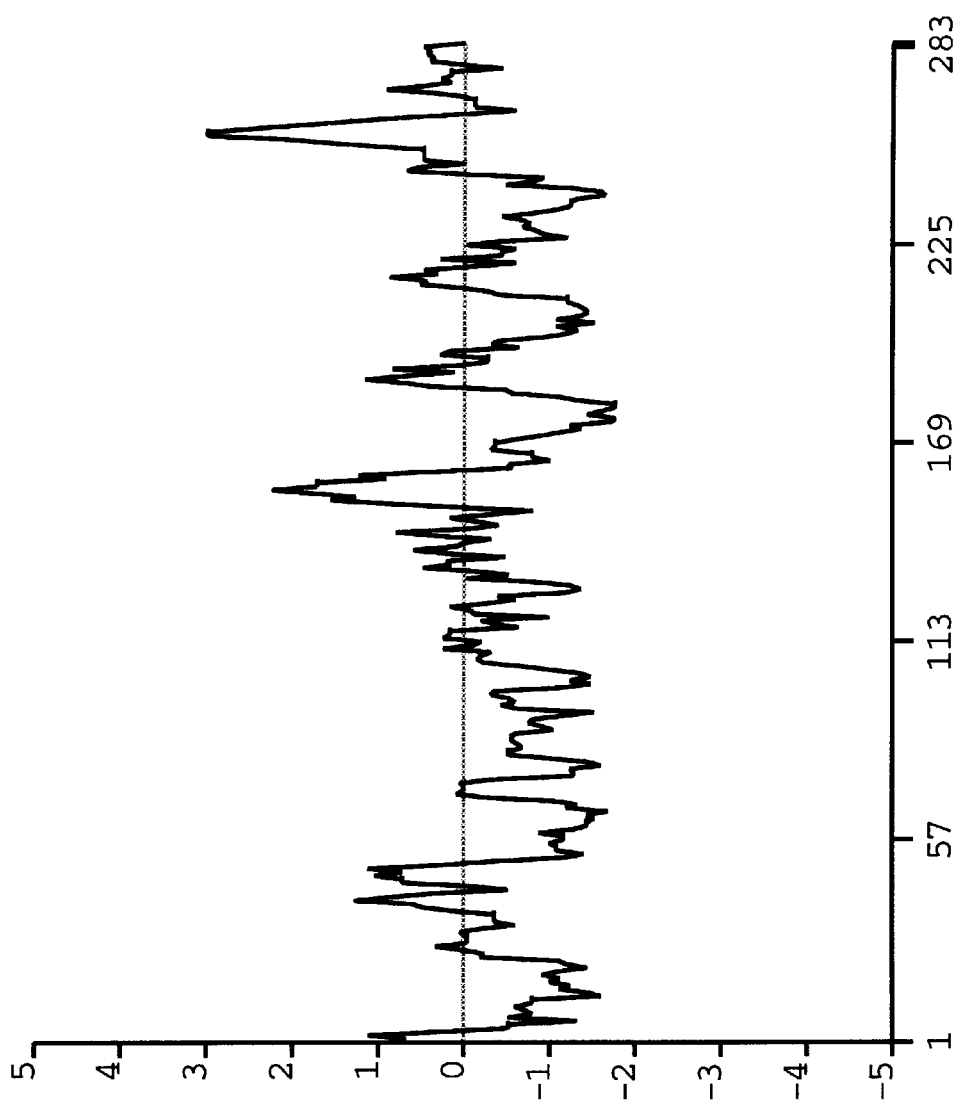

In one embodiment, the invention encompasses a polypeptide comprising the amino acid sequence of SEQ ID NO:1, as shown in FIGS. 1A, 1B, 1C, and 1D. HPA-l is 285 amino acids in length and has three potential casein kinase II phosphorylation sites at residues $S_{115}$, $S_{256}$, and $T_{268}$; one potential N-glycosylation site at residue $N_{143}$; and one potential protein kinase C phosphorylation site at reside $F_{256}$. As shown in FIG. 2, HPA-1 has chemical and structural homology with phosphatidic acid phosphatase (GI 1487873; SEQ ID NO:3) etc. In particular, HPA-1 and phosphatidic acid phosphatase share 72% identity, and the casein kinase II phosphorylation sites at residues $S_{115}$ and $T_{268}$. As illustrated by FIGS. 3A and 3B, HPA-1 and phosphatidic acid phosphatase have rather similar hydrophobicity plots. Northern analysis shows the expression of this sequence in various libraries, at least 48% of which are immortalized or cancerous and at least 25% of which involve immune response.

Nucleic acids encoding the HPA-2 of the present invention were first identified in Incyte Clone 1734452 from the gastrointestinal cDNA library (COLNNOT22) using a computer search for amino acid sequence alignments. A consensus sequence, SEQ ID NO:2, was derived from the following overlapping and/or extended nucleic acid sequences: Incyte Clones 1734452 (COLNNOT22), 2099466 (BRAITUT02), 1528322 (UCMCL5T01), 809256 (LUNGNOT04), 887202 (PANCNOT05), 1851186 (LUNGFET03), 513145 (MPHGNOT03), 1676421 (BLADNOT05), and 1443485 (THYRNOT03).

Figure 6A:
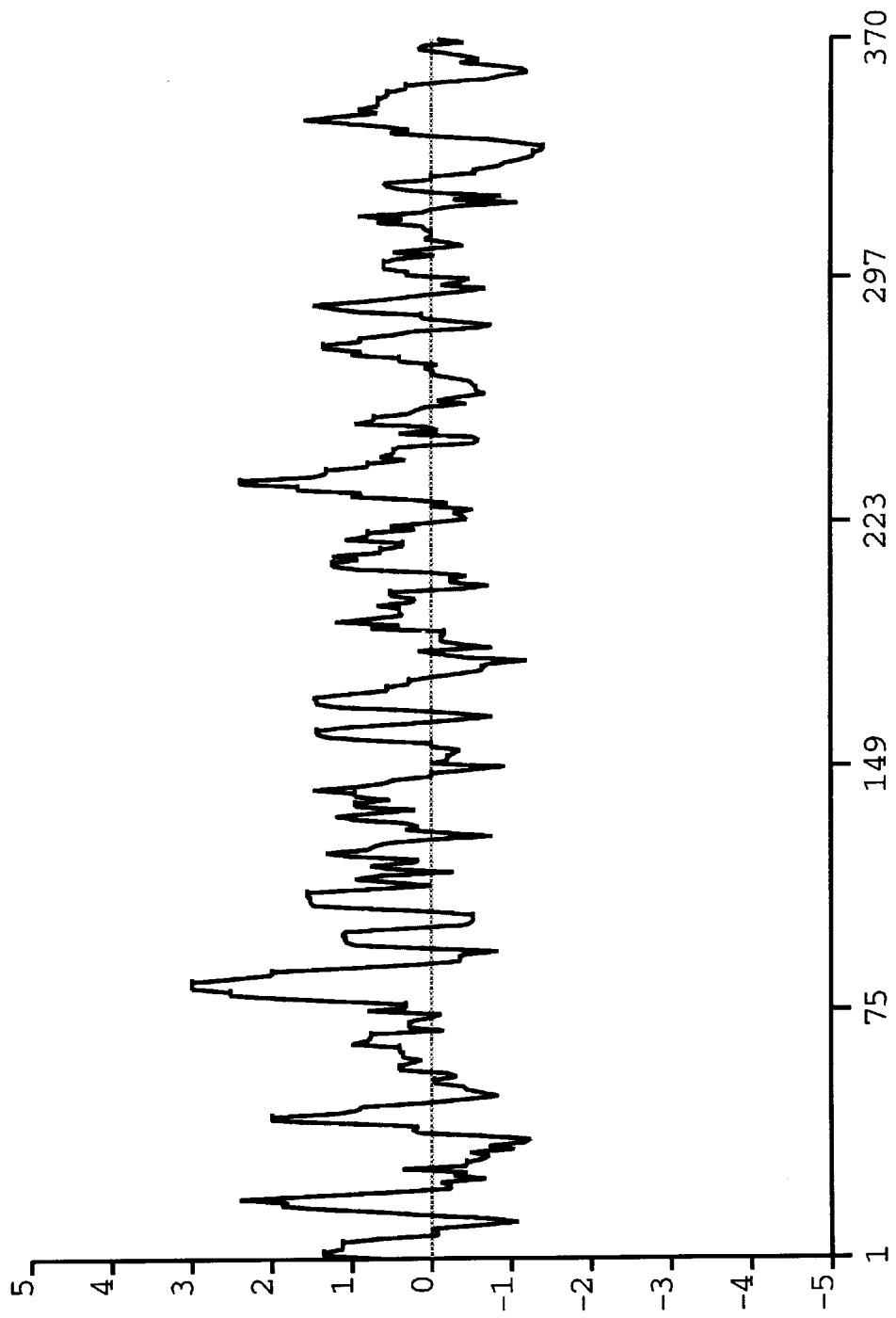
FIGS. 6A and 6B show the hydrophobicity plots for HPA-2, SEQ ID NO:4 and Rp47 (SEQ ID NO:6), respectively; the positive X axis reflects amino acid position, and the negative Y axis, hydrophobicity (MacDNASIS PRO software).
Figure 6B:
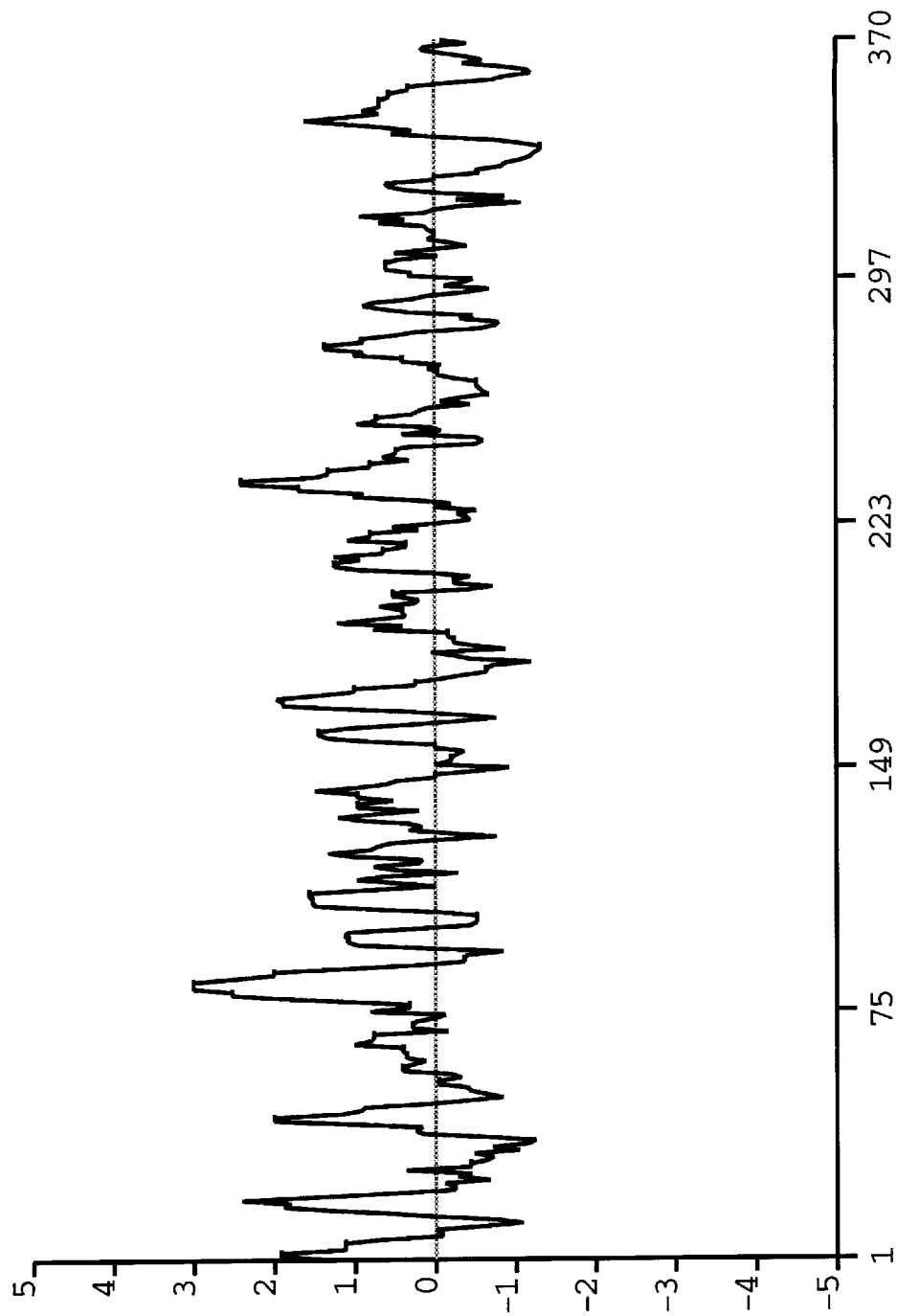

In one embodiment, the invention encompasses a polypeptide comprising the amino acid sequence of SEQ ID NO:4, as shown in FIGS. 4A, 4B, 4C, 4D, 4E, 4F, and 4G. HPA-2 is 370 amino acids in length and has a potential cAMP- and cGMP-dependent protein kinase phosphorylation site at residue $S_{111}$; one potential N-glycosylation site at residue $N_{313}$; eight potential casein kinase II phosphorylation sites at residues $T_{16}$, $S_{40}$, $S_{74}$, $S_{114}$ $S_{140}$, $S_{176}$, $S_{200}$, and $T_{354}$; and six protein kinase C phosphorylation sites at residues $S_{74}$, $S_{99}$, $T_{144}$, $S_{212}$, $S_{315}$, and $T_{354}$. As shown in FIG. 5, HPA-2 has chemical and structural homology with p47 (GI 2285790; SEQ ID NO:6). In particular, HPA-2 and p47-phox share 96% identity, the cAMP- and cGMP-dependent protein kinase phosphorylation site, six of the casein kinase II phosphorylation sites, and all of the protein C phosphorylation sites. As illustrated by FIGS. 6A and 6B, HPA-2 and p47 have rather similar hydrophobicity plots. Northern analysis shows the expression of this sequence in various libraries, at least 51% of which are immortalized or cancerous and at least 21% of which involve immune response.

The invention also encompasses HPA variants. A preferred HPA variant is one having at least 80%, and more preferably at least 90%, amino acid sequence identity to the HPA amino acid sequence (SEQ ID NO:1) and which retains at least one biological, immunological or other functional characteristic or activity of HPA. A most preferred HPA variant is one having at least 95% amino acid sequence identity to SEQ ID NO:1.

The invention also encompasses a polynucleotide sequence which encodes HPA. Accordingly, any nucleic acid sequence which encodes the amino acid sequence of HPA can be used to produce recombinant molecules which express HPA. In a particular embodiment, the invention encompasses the polynucleotide comprising the nucleic acid sequence of SEQ ID NO:2 as shown in FIGS. 1A,1B,1C, and 1D. In a particular embodiment, the invention encompasses the polynucleotide comprising the nucleic acid sequence of SEQ ID NO:5 as shown in FIGS. 4A, 4B, 4C, 4D, 4E, 4F, and 4G.

The invention also encompasses a variant of a polynucleotide sequence encoding HPA. In particular, such a variant polynucleotide sequence will have at least about 80%, more preferably at least about 90%, and most preferably at least about 95% polynucleotide sequence identity to the polynucleotide sequence encoding HPA. A particular aspect of the invention encompasses a variant of SEQ ID NO:2 which has about 80%, more preferably at least about 90%, and most preferably at least about 95% polynucleotide sequence identity to SEQ ID NO:2. A particular aspect of the invention encompasses a variant of SEQ ID NO:5 which has about 80%, more preferably at least about 90%, and most preferably at least about 95% polynucleotide sequence identity to SEQ ID NO:5.

It will be appreciated by those skilled in the art that as a result of the degeneracy of the genetic code, a multitude of nucleotide sequences encoding HPA, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring HPA, and all such variations are to be considered as being specifically disclosed.

Although nucleotide sequences which encode HPA and its variants are preferably capable of hybridizing to the nucleotide sequence of the naturally occurring HPA under appropriately selected conditions of stringency, it may be advantageous to produce nucleotide sequences encoding HPA or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HPA and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode HPA and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding HPA or any fragment thereof.

Also encompassed by the invention are polynucleotide sequences that are capable of hybridizing to the claimed nucleotide sequences, and in particular, those shown in SEQ ID NO:2 and SEQ ID NO:5, under various conditions of stringency as taught in Wahl, G. M. and S. L. Berger (1987) Methods Enzymol. 152:399–407; and Kimmel, A. R. (1987) Methods Enzymol. 152:507–511.

Methods for DNA sequencing which are well known and generally available in the art and may be used to practice any of the embodiments of the invention. The methods may employ such enzymes as the Klenow fragment of DNA polymerase I, Sequenase® (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding HPA may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 Primer Analysis software (National Biosciences Inc., Plymouth, MN), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991) Nucleic Acids Res. 19:3055–3060. Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. Genotyper™ and Sequence Navigator™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HPA may be used in recombinant DNA molecules to direct expression of HPA, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express HPA.

As will be understood by those of skill in the art, it may be advantageous to produce HPA-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter HPA encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding HPA may be ligated to a heterologous sequence to encode a fusion protein. For example, to screen peptide libraries for inhibitors of HPA activity, it may be useful to encode a chimeric HPA protein that can be recognized by a commercially available antibody. A fusion protein may also be engineered to contain a cleavage site located between the HPA encoding sequence and the heterologous protein sequence, so that HPA may be cleaved and purified away from the heterologous moiety.

In another embodiment, sequences encoding HPA may be synthesized, in whole or in part, using chemical methods well known in the art (see, e.g. Caruthers, M. H. et al. (1980) Nucl. Acids Res. Symp. Ser. 215–223; and Horn, T. et al. (1980) Nucl. Acids Res. Symp. Ser. 225–232). Alternatively, the protein itself may be produced using chemical methods to synthesize the amino acid sequence of HPA, or a fragment thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) Proteins, Structures and Molecular Principles, WH Freeman and Co., New York, N.Y.). The composition of the synthetic peptides may be confirmed by amino acid analysis or sequencing (e.g., the Edman degradation procedure; Creighton, supra). Additionally, the amino acid sequence of HPA, or any part thereof, may be altered during direct synthesis and/or combined using chemical methods with sequences from other proteins, or any part thereof, to produce a variant polypeptide.

In order to express a biologically active HPA, the nucleotide sequences encoding HPA or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding HPA and appropriate transcriptional and translational control elements. These methods include in vitro recombinant DNA techniques, synthetic techniques, and in vivo genetic recombination. Such techniques are described, e.g., in Sambrook, J. et al. (1989) Molecular Cloning, A Laboratory Manual, Cold Spring Harbor Press, Plainview, N.Y., and Ausubel, F.M. et al. (1989) Current Protocols in Molecular Biology, John Wiley & Sons, New York, N.Y.

A variety of expression vector/host systems may be utilized to contain and express sequences encoding HPA. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HPA, vectors based on SV40 or EBV may be used with an appropriate selectable marker.

In bacterial systems, a number of expression vectors may be selected depending upon the use intended for HPA. For example, when large quantities of HPA are needed for the induction of antibodies, vectors which direct high level expression of fusion proteins that are readily purified may be used. Such vectors include, but are not limited to, the multifunctional *E. coli* cloning and expression vectors such as Bluescript® (Stratagene), in which the sequence encoding HPA may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Meth. Enzymol. 153:516–544.

In cases where plant expression vectors are used, the expression of sequences encoding HPA may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191–196.

An insect system may also be used to express HPA. For example, in one such system, *Autographa californica* nuclear polyhedrosis virus (AcNPV) is used as a vector to express foreign genes in *Spodoptera frugiperda* cells or in *Trichoplusia larvae*. The sequences encoding HPA may be cloned into a non-essential region of the virus, such as the polyhedrin gene, and placed under control of the polyhedrin promoter. Successful insertion of HPA will render the polyhedrin gene inactive and produce recombinant virus lacking coat protein. The recombinant viruses may then be used to infect, for example, *S. frugiperda* cells or *Trichoplusia larvae* in which HPA may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding HPA may be ligated into an adenovirus transcription/translation complex consisting of the late promoter and tripartite leader sequence. Insertion in a non-essential E1 or E3 region of the viral genome may be used to obtain a viable virus which is capable of expressing HPA in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding HPA. Such signals include the ATG initiation codon and adjacent sequences. In cases where sequences encoding HPA, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express HPA may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk- or aprt- cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Meth. Mol. Biol. 55:121–131).

Although the presence/absence of marker gene expression suggests that the gene of interest is also present, its presence and expression may need to be confirmed. For example, if the sequence encoding HPA is inserted within a marker gene sequence, transformed cells containing sequences encoding HPA can be identified by the absence of marker gene function. Alternatively, a marker gene can be placed in tandem with a sequence encoding HPA under the control of a single promoter. Expression of the marker gene in response to induction or selection usually indicates expression of the tandem gene as well.

Alternatively, host cells which contain the nucleic acid sequence encoding HPA and express HPA may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding HPA can be detected by DNA-DNA or DNA-RNA hybridization or amplification using probes or fragments or fragments of polynucleotides encoding HPA. Nucleic acid amplification based assays involve the use of oligonucleotides or oligomers based on the sequences encoding HPA to detect transformants containing DNA or RNA encoding HPA.

A variety of protocols for detecting and measuring the expression of HPA, using either polyclonal or monoclonal antibodies specific for the protein are known in the art.

Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on HPA is preferred, but a competitive binding assay may be employed. These and other assays are described, among other places, in Hampton, R. et al. (1990; Serological Methods, a Laboratory Manual, APS Press, St Paul, Minn.; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HPA include oligolabeling, nick translation, end-labeling or PCR amplification using a labeled nucleotide. Alternatively, the sequences encoding HPA, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison, Wis.); and U.S. Biochemical Corp., Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding HPA may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode HPA may be designed to contain signal sequences which direct secretion of HPA through a prokaryotic or eukaryotic cell membrane. Other constructions may be used to join sequences encoding HPA to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and HPA may be used to facilitate purification. One such expression vector provides for expression of a fusion protein containing HPA and a nucleic acid encoding 6 histidine residues preceding a thioredoxin or an enterokinase cleavage site. The histidine residues facilitate purification on IMAC (immobilized metal ion affinity chromatography as described in Porath, J. et al. (1992, Prot. Exp. Purif. 3: 263–281) while the enterokinase cleavage site provides a means for purifying HPA from the fusion protein. A discussion of vectors which contain fusion proteins is provided in Kroll, D. J. et al. (1993; DNA Cell Biol. 12:441–453).

In addition to recombinant production, fragments of HPA may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of HPA may be chemically synthesized separately and combined using chemical methods to produce the full length molecule.

THERAPEUTICS

Chemical and structural homology exists between HPA-1 and phosphatidic acid phosphatase from mouse (GI 1487873; SEQ ID NO:3), and between HPA-2 and p47-phox from rat (GI 2285789; SEQ ID NO:6). Northern analysis shows that the expression of HPA (SEQ ID NO:1 or SEQ ID NO:4) in tissues associated with immune disorders and diseases associated with cancer.

Therefore, in one embodiment, an antagonist of HPA or a fragment or derivative thereof may be administered to a subject to treat or prevent a cancer. Such cancers may include, but are not limited to, adenocarcinoma, leukemia, lymphoma, melanoma, myeloma, sarcoma, and teratocarcinoma; and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds HPAC may be used directly as an antagonist or indirectly as a targeting or delivery mechanism for bringing a pharmaceutical agent to cells or tissues which express HPA. In another embodiment, an antagonist of HPA may be administered to a subject to prevent or treat an immune disorder. Such disorders may include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma.

In another embodiment, a vector expressing the complement of the polynucleotide encoding HPA may be administered to a subject to treat or prevent the disorders including, but not limited to, those described above.

Therefore, in one embodiment, an antagonist of HPA may be administered to a subject to prevent or treat an immune disorder. Immune disorders may include, but are not limited to AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, and extracorporeal circulation; viral, bacterial, fungal, parasitic, protozoal, and helminthic infections; and trauma. In one aspect, an antibody which specifically binds HPA may be used directly as an antagonist or indirectly as a targeting or delivery mechanism for bringing a pharmaceutical agent to cells or tissues which express HPA.

In another embodiment, a vector expressing the complement of the polynucleotide encoding HPA may be administered to a subject to treat or prevent an immune disorder including, but not limited to, the disorders described above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HPA may be produced using methods which are generally known in the art. In particular, purified HPA may be used to produce antibodies or to screen libraries of pharmaceutical agents to identify those which specifically bind HPA.

Antibodies to HPA may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with HPA or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HPA have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of HPA amino acids may be fused with those of another protein such as keyhole limpet hemocyanin and antibody produced against the chimeric molecule.

Monoclonal antibodies to HPA may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454). Alternatively, techniques described for the production of single chain antibodies may be adapted, using methods known in the art, to produce HPA-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; and Winter, G. et al. (1991) Nature 349:293–299).

Antibody fragments which contain specific binding sites for HPA may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HPA and its specific antibody. A two-site, monoclonal-based immunoassay utilizing monoclonal antibodies reactive to two non-interfering HPA epitopes is preferred, but a competitive binding assay may also be employed (Maddox, supra).

In another embodiment of the invention, the polynucleotides encoding HPA, or any fragment or complement thereof, may be used for therapeutic purposes. In one aspect, the complement of the polynucleotide encoding HPA may be used in situations in which it would be desirable to block the transcription of the mRNA. In particular, cells may be transformed with sequences complementary to polynucleotides encoding HPA. Thus, complementary molecules or fragments may be used to modulate HPA activity, or to achieve regulation of gene function. Such technology is now well known in the art, and sense or antisense oligonucleotides or larger fragments, can be designed from various locations along the coding or control regions of sequences encoding HPA.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding HPA. These techniques are described both in Sambrook et al. (supra) and in Ausubel et al. (supra).

Genes encoding HPA can be turned off by transforming a cell or tissue with expression vectors which express high levels of a polynucleotide or fragment thereof which encodes HPA. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding HPA (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, Molecular and Immunologic Approaches, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding HPA.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HPA. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of HPA, antibodies to HPA, mimetics, agonists, antagonists, or inhibitors of HPA. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of HPA, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example HPA or fragments thereof, antibodies of HPA, agonists, antagonists or inhibitors of HPA, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind HPA may be used for the diagnosis of conditions or diseases characterized by expression of HPA, or in assays to monitor patients being treated with HPA, agonists, antagonists or inhibitors. The antibodies useful for diagnostic purposes may be prepared in the same manner as those described above for therapeutics. Diagnostic assays for HPA include methods which utilize the antibody and a label to detect HPA in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring HPA are known in the art and provide a basis for diagnosing altered or abnormal levels of HPA expression. Normal or standard values for HPA expression are established by combining body fluids or cell extracts taken from normal mammalian subjects, preferably human, with antibody to HPA under conditions suitable for complex formation The amount of standard complex formation may be quantified by various methods, but preferably by photometric means. Quantities of HPA expressed in subject samples, control samples, and disease samples from biopsied tissues are compared with the standard values. Deviation between standard and subject values establishes the parameters for diagnosing disease.

In another embodiment of the invention, the polynucleotides encoding HPA may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HPA may be correlated with disease. The diagnostic assay may be used to distinguish between absence, presence, and excess expression of HPA, and to monitor regulation of HPA levels during therapeutic intervention.

In one aspect, hybridization with PCR probes which are capable of detecting polynucleotide sequences, including genomic sequences, encoding HPA or closely related molecules, may be used to identify nucleic acid sequences which encode HPA. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding HPA, alleles, or related sequences.

Probes may also be used for the detection of related sequences, and should preferably contain at least 50% of the nucleotides from any of the HPA encoding sequences. The hybridization probes of the subject invention may be DNA or RNA and derived from the nucleotide sequence of SEQ ID NO:2 and SEQ ID NO:5 or from genomic sequence including promoter, enhancer elements, and introns of the naturally occurring HPA.

Means for producing specific hybridization probes for DNAs encoding HPA include the cloning of nucleic acid sequences encoding HPA or HPA derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Examples of such conditions or disorders include, but are not limited to, cancers such as adenocarcinoma, leukemia, lymphoma, melanoma, myeloma, sarcoma, and teratocarcinoma; and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and immune disorders such as AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, and extracorporeal circulation; viral, bacterial, fungal, parasitic, protozoal, and helminthic infections; and trauma. The polynucleotide sequences encoding HPA may be used in Southern or northern analysis, dot blot, or other membrane-based technologies; in PCR technologies; or in dipstick, pin, ELISA assays or microarrays utilizing fluids or tissues from patient biopsies to detect altered HPA expression. Such qualitative or quantitative methods are well known in the art.

In a particular aspect, the nucleotide sequences encoding HPA may be useful in assays that detect activation or induction of various cancers, particularly those mentioned above. The nucleotide sequences encoding HPA may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding HPA in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of HPA, a normal or standard profile for expression is established. This may be accomplished by combining body fluids or cell extracts taken from normal subjects, either animal or human, with a sequence, or a fragment thereof, which encodes HPA, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HPA may involve the use of PCR. Such oligomers may be chemically synthesized, generated enzymatically, or produced in vitro. Oligomers will preferably consist of two nucleotide sequences, one with sense orientation (5'>3') and another with antisense (3'<–5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of HPA include radiolabeling or biotinylating nucleotides, coamplification of a control nucleic acid, and standard curves onto which the experimental results are interpolated (Melby, P. C. et al. (1993) J. Immunol. Meth. 159:235–244; and Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Natl. Acad. Sci. 94:2150–55).

In one embodiment, the microarray is prepared and used according to the methods described in PCT application WO95/11995 (Chee et al.), Lockhart, D. J. et al. (1996) Nat. Biotech. 14: 1675–1680; and Schena, M. et al. (1996) Proc. Natl. Acad. Sci. 93: 10614–10619.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode HPA may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial PI constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH) as described in Verma et al. (1988) Human Chromosomes: A Manual of Basic Techniques, Pergamon Press, New York, N.Y. may be correlated with other physical chromosome mapping techniques and genetic map data. Examples of genetic map data can be found in various scientific journals or at Online Mendelian Inheritance in Man (OMIM). Correlation between the location of the gene encoding HPA on a physical chromosomal map and a specific disease , or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, HPA, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between HPA and the agent being tested, may be measured.

Another technique for drug screening which may be used provides for high throughput screening of compounds having suitable binding affinity to the protein of interest as described in published PCT application W084/03564. In this method, as applied to HPA large numbers of different small test compounds are synthesized on a solid substrate, such as plastic pins or some other surface. The test compounds are reacted with HPA, or fragments thereof, and washed. Bound HPA is then detected by methods well known in the art. Purified HPA can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HPA specifically compete with a test compound for binding HPA. In this manner, the antibodies can be used to detect the presence of any peptide which shares one or more antigenic determinants with HPA.

In additional embodiments, the nucleotide sequences which encode HPA may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction

BLADNOT06

The BLADNOT06 cDNA libraries was constructed from microscopically normal bladder tissue and associated bladder tumor tissue obtained from a 66-year-old Caucasian male during a radical cystectomy, radical prostatectomy, and urinary diversion. Nontumorous tissue (BLADNOT06) was removed from the posterior wall of the bladder. This was also associated with a grade 3 transitional cell carcinoma of the prostate and prostatic urethra, with diffuse invasion to the prostatic parenchyma anteriorly and posteriorly. Surgical margins and multiple pelvic lymph nodes were negative for tumor. The patient presented with prostatic inflammatory disease. Patient history inclued a transurethral prostatectomy, lung neoplasm, benign hypertension, and tobacco use. Family history included a malignant breast neoplasm in the mother, tuberculosis in the father, a malignant lung neoplasm in a sibling, and hypertension, cerebrovascular disease, and arteriosclerotic coronary artery diseasae in another sibling.

COLNNOT22

The COLNNOT22 library was constructed from microscopically normal colon tissue excised from a 56-year-old Caucasian female during a resection of the small intestine. The patient was diagnosed with Crohn's disease involving the ileum and ileal-colonic anastomosis. The patient history included a cholecystectomy and breast lesions. Family history included atherosclerosis in a grandparent and functional disorder of the intestine in the patient's mother.

BLADNOT06 & COLNNOT22

The frozen tissue was homogenized and lysed using a Brinkmann Homogenizer Polytron PT-3000 (Brinkmann Instruments, Westbury, N.J.) in guanidinium isothiocyanate solution. The lysate was centrifuged over a 5.7 M CsCl cushion using an Beckman SW28 rotor in a Beckman L8–70M Ultracentrifuge (Beckman Instruments) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and DNase treated at 37° C. The RNA extraction was repeated with acid phenol pH 4.7 and precipitated with sodium acetate and ethanol as before. The mRNA was then isolated using the Qiagen Oligotex kit (QIAGEN, Inc., Chatsworth, Calif.) and used to construct the cDNA library.

The mRNA was handled according to the recommended protocols in the SuperScript Plasmid System for cDNA Synthesis and Plasmid Cloning (Cat. #18248–013, Gibco/BRL).The cDNAs were fractionated on a Sepharose CL4B column (Cat. #275105–01; Pharmacia), and those cDNAs exceeding 400 bp were ligated into pINCY 1. The plasmid pINCY 1 was subsequently transformed into DH5a™ competent cells (Cat. #18258–012; Gibco/BRL).

II Isolation and Sequencing of cDNA Clones

Plasmid DNA was released from the cells and purified using the REAL Prep 96 Plasmid Kit for Rapid Extraction Alkaline Lysis Plasmid Minipreps (Catalog #26173; QIAGEN, Inc.). This kit enabled the simultaneous purification of 96 samples in a 96-well block using multi-channel reagent dispensers. The recommended protocol was employed except for the following changes:1) the bacteria were cultured in 1 ml of sterile Terrific Broth (Catalog #22711, GIBCO/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems.

III Homology Searching of cDNA Clones and Their Deduced Proteins

After the reading frame was determined, the nucleotide sequences of the Sequence Listing or amino acid sequences deduced from them were used as query sequences against databases such as GenBank, SwissProt, BLOCKS, and Pima II. These databases which contain previously identified and annotated sequences, were searched for regions of homology (similarity) using BLAST, which stands for Basic Local Alignment Search Tool (Altschul (1993) supra, Altschul (1990) supra).

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST (Basic Local Alignment Search Tool). (Altschul, S. F. (1993) J. Mol. Evol 36:290–300; Altschul et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms such as the one described in Smith, T. et al. (1992) Prot. Eng. 5:35–51), could have been used when dealing with primary sequence patterns and secondary structure gap penalties. The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-10}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for homology.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993) J.Mol.Evol. 36:290–300; Altschul, S. F. et al. (1990) J.Mol.Evol. 215:403–410) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

% sequence identity×% maximum BLAST score/100

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding HPA occurs. Abundance and percent abundance are also reported. Abundance directly reflects the number of times a particular transcript is represented in a cDNA library, and percent abundance is abundance divided by the total number of sequences examined in the cDNA library.

V Extension of HPA Encoding Polynucleotides

The nucleic acid sequences of the Incyte Clones 1719418 and 1734452 were used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier Thermal Cycler (PTC200; M.J. Research, Watertown, Mass.) and the following parameters:

| Step 1 | 94° C. for 1 min (initial denaturation) |
|---|---|
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQuick™ (QIAGEN), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2–3 hours or overnight at 16° C. Competent E. coli cells (in 40 μl of appropriate media) were transformed with 3 μl of ligation mixture and cultured in 80 μl of SOC medium (Sambrook et al., supra). After incubation for one hour at 37° C., the E. coli mixture was plated on Luria Bertani (LB)-agar (Sambrook et al., supra) containing 2x Carb. The following day, several colonies were randomly picked from each plate and cultured in 150 µl of liquid LB/2x Carb medium placed in an individual well of an appropriate, commercially-available, sterile 96-well microtiter plate. The following day, 5 µl of each overnight culture was transferred into a non-sterile 96-well plate and after dilution 1:10 with water, 5 µl of each sample was transferred into a PCR array.

For PCR amplification, 18 µl of concentrated PCR reaction mix (3.3x) containing 4 units of rTth DNA polymerase, a vector primer, and one or both of the gene specific primers used for the extension reaction were added to each well. Amplification was performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 µCi of [$\gamma$-$^{32}$P] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1x saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the HPA-encoding sequence, or any part thereof, is used to decrease or inhibit expression of naturally occurring HPA. Although use of oligonucleotides comprising from about 15 to about 30 base-pairs is described, essentially the same procedure is used with smaller or larger sequence fragments. Appropriate oligonucleotides are designed using Oligo 4.06 software and the coding sequence of HPA, SEQ ID NO:1. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HPA-encoding transcript.

IX Expression of HPA

Expression of HPA is accomplished by subcloning the cDNAs into appropriate vectors and transforming the vectors into host cells. In this case, the cloning vector is also used to express HPA in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of HPA into the bacterial growth media which can be used directly in the following assay for activity.

X Demonstration of HPA Activity

Reaction mixtures (150 ul total) contain 50 mM $N_aPO_4$ (pH 7.0), 1 mM EGTA, 5 mM $MgCl_2$ plus one of the following: a combination of the cytosolic and membrane fractions (25:1 protein:protein ratio), the cytosolic fraction only, the membrane fraction only, partially purified enzyme, or column fractions. GST-p47-phox (1 ug/reaction) or recombinant p47-phox (Rp47, 1 ug/reaction) is added to the mixtures. Six ul of [gamma-$^{32}$P]ATP is added, followed by the immediate addition of activator. This mixture is allowed to incubate at 25° C. for 45 min. The reaction was then terminated by the addition of Laemrnli sample buffer and prepared for SDS-PAGE analysis. Proteins are separated by 8–15% SDS-PAGE, silver stained, dried, and analyzed via autoradiography. Protein kinase inhibitors are added 5 min prior to the addition of [gamma-$^{32}$P]ATP. For samples that are analyzed by western blotting, reactions are preformed as above with the following modifications; Cold ATP (10 ul) is used in place of radiolabeled ATP. Proteins are separated by 9% SDS-PAGE and then transferred to polyvinylidene difluoride (Kristin, A. W. (1997) J. Biol. Chem. 272 (24):15569–15578).

XI Production of HPA Specific Antibodies

HPA that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431 A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring HPA Using Specific Antibodies

Naturally occurring or recombinant HPA is substantially purified by immunoaffinity chromatography using antibodies specific for HPA. An immunoaffinity column is constructed by covalently coupling HPA antibody to an activated chromatographic resin, such as CNBr-activated Sepharose (Pharmacia & Upjohn). After the coupling, the resin is blocked and washed according to the manufacturer's instructions.

Media containing HPA is passed over the immunoaffinity column, and the column is washed under conditions that allow the preferential absorbance of HPA (e.g., high ionic strength buffers in the presence of detergent). The column is eluted under conditions that disrupt antibody/HPA binding (eg, a buffer of pH 2–3 or a high concentration of a chaotrope, such as urea or thiocyanate ion), and HPA is collected.

XIII Identification of Molecules Which Interact with HPA

HPA or biologically active fragments thereof are labeled with $^{125}$I Bolton-Hunter reagent (Bolton et al. (1973) Biochem. J. 133:529). Candidate molecules previously arrayed in the wells of a multi-well plate are incubate with the labeled HPA, washed and any wells with labeled HPA complex are assayed. Data obtained using different concentrations of HPA are used to calculate values for the number, affinity, and association of HPA with the candidate molecules.

Alternatively HPA-associated molecules are isolated using a two-hybrid system as described in Fields, S and Sternglanz, R (1994) Trends. Genet. 10:286–292.

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claim.

What is claimed is:

1. An isolated and purified polynucleotide sequence encoding the human phosphatase (HPA) of SEQ ID NO:1.

2. A composition comprising the polynucleotide sequence of claim 1.

3. An isolated and purified polynucleotide sequence which is completely complementary to the polynucleotide sequence of claim 1.

4. An isolated and purified polynucleotide sequence comprising SEQ ID NO:2.

5. An isolated and purified polynucleotide sequence which is completely complementary to the polynucleotide sequence of claim 4.

6. An expression vector containing the polynucleotide sequence of claim 1.

7. A host cell containing the expression vector of claim 6.

8. A method for producing a polypeptide comprising the amino acid sequence of SEQ ID NO:1, the method comprising the steps of:

a) culturing the host cell of claim 7 under conditions suitable for the expression of the polypeptide; and b) recovering the polypeptide from the host cell culture.

9. A method for detecting a polynucleotide encoding HPA in a biological sample containing nucleic acids, the method comprising the steps of:

(a) hybridizing the polynucleotide of claim 3 under high stringency conditions to at least one of the nucleic acids in the biological sample, thereby forming a hybridization complex; and (b) detecting the hybridization complex, wherein the presence of the hybridization complex correlates with the presence of a polynucleotide encoding HPA in the biological sample.

10. The method of claim 9 wherein the nucleic acids of the biological sample are amplified by the polymerase chain reaction prior to hybridization.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 285 amino acids
      (B) TYPE: amino acid
      (C) STRANDEDNESS: single
      (D) TOPOLOGY: linear (vii) IMMEDIATE SOURCE:
      (A) LIBRARY: BLADNOT06
      (B) CLONE: 1719418

(xi) SEQUENCE DESCRIPTION: SEQ ID NO:1:

Met Phe Asp Lys Thr Arg Leu Pro Tyr Val Ala Leu Asp Val Leu Cys
 1            5               10              15

```
Val Leu Leu Ala Ser Met Pro Met Ala Val Leu Lys Leu Gly Gln Ile
             20                  25                  30

Tyr Pro Phe Gln Arg Gly Phe Phe Cys Lys Asp Asn Ser Ile Asn Tyr
             35                  40                  45

Pro Tyr His Asp Ser Thr Val Thr Ser Thr Val Leu Ile Leu Val Gly
 50                  55                  60

Val Gly Leu Pro Ile Ser Ser Ile Ile Leu Gly Glu Thr Leu Ser Val
 65                  70                  75                  80

Tyr Cys Asn Leu Leu His Ser Asn Ser Phe Ile Arg Asn Asn Tyr Ile
                 85                  90                  95

Ala Thr Ile Tyr Lys Ala Ile Gly Thr Phe Leu Phe Gly Ala Ala Ala
             100                 105                 110

Ser Gln Ser Leu Thr Asp Ile Ala Lys Tyr Ser Ile Gly Arg Leu Arg
             115                 120                 125

Pro His Phe Leu Asp Val Cys Asp Pro Asp Trp Ser Lys Ile Asn Cys
 130                 135                 140

Ser Asp Gly Tyr Ile Glu Tyr Tyr Ile Cys Arg Gly Asn Ala Glu Arg
 145                 150                 155                 160

Val Lys Glu Gly Arg Leu Ser Phe Tyr Ser Gly His Ser Ser Phe Ser
                 165                 170                 175

Met Tyr Cys Met Leu Phe Val Ala Leu Tyr Leu Gln Ala Arg Met Lys
             180                 185                 190

Gly Asp Trp Ala Arg Leu Leu Arg Pro Thr Leu Gln Phe Gly Leu Val
             195                 200                 205

Ala Val Ser Ile Tyr Val Gly Leu Ser Arg Val Ser Asp Tyr Lys His
 210                 215                 220

His Trp Ser Asp Val Leu Thr Gly Leu Ile Gln Gly Ala Leu Val Ala
225                 230                 235                 240

Ile Leu Val Ala Val Tyr Val Ser Asp Phe Phe Lys Glu Arg Thr Ser
                 245                 250                 255

Phe Lys Glu Arg Lys Glu Glu Asp Ser His Thr Thr Leu His Glu Thr
             260                 265                 270

Pro Thr Thr Gly Asn His Tyr Pro Ser Asn His Gln Pro
             275                 280                 285

(2) INFORMATION FOR SEQ ID NO:2:

(i) SEQUENCE CHARACTERISTICS:
        (A) LENGTH: 1315 base pairs
        (B) TYPE: nucleic acid
        (C) STRANDEDNESS: single
        (D) TOPOLOGY: linear (vii) IMMEDIATE SOURCE:
        (A) LIBRARY: BLADNOT06
        (B) CLONE: 1719418

(xi) SEQUENCE DESCRIPTION: SEQ ID NO:2:

NNTCGCCAGC CCCGGCCCGG GCTCGAGAAT CAAGGGCCTC GGCCGCCGTC CCGCAGCTCA      60

GTCCATCGCC CTTGCCGGGC AGCCCGGGCA GAGACCATGT TTGACAAGAC GCGGCTGCCG     120

TACGTGGCCC TCGATGTGCT CTGCGTGTTG CTGGCTTCCA TGCCTATGGC TGTTCTAAAA     180

TTGGGCCAAA TATATCCATT TCAGAGAGGC TTTTTCTGTA AAGACAACAG CATCAACTAT     240

CCGTACCATG ACAGTACCGT CACATCCACT GTCCTCATCC TAGTGGGGGT TGGCTTGCCC     300

ATTTCCTCTA TTATTCTTGG AGAAACCCTG TCTGTTTACT GTAACCTTTT GCACTCAAAT     360

TCCTTTATCA GGAATAACTA CATAGCCACT ATTTACAAAG CCATTGGAAC CTTTTTATTT     420
```

```
GGTGCAGCTG CTAGTCAGTC CCTGACTGAC ATTGCCAAGT ATTCAATAGG CAGACTGCGG      480

CCTCACTTCT TGGATGTTTG TGATCCAGAT TGGTCAAAAA TCAACTGCAG CGATGGTTAC      540

ATTGAATACT ACATATGTCG AGGGAATGCA GAAAGAGTTA AGGAAGGCAG GTTGTCCTTC      600

TATTCAGGCC ACTCTTCGTT TTCCATGTAC TGCATGCTGT TTGTGGCACT TTATCTTCAA      660

GCCAGGATGA AGGGAGACTG GGCAAGACTC TTACGCCCCA CACTGCAATT TGGTCTTGTT      720

GCCGTATCCA TTTATGTGGG CCTTTCTCGA GTTTCTGATT ATAAACACCA CTGGAGCGAT      780

GTGTTGACTG GACTCATTCA GGGAGCTCTG GTTGCAATAT TAGTTGCTGT ATATGTATCG      840

GATTTCTTCA AGAAAGAAC TTCTTTTAAA GAAAGAAAAG AGGAGGACTC TCATACAACT       900

CTGCATGAAA CACCAACAAC TGGGAATCAC TATCCGAGCA ATCACCAGCC TTGAAAGGCA      960

GCAGGGTGCC CAGGTGAAGC TGGCCTGTTT TCTAAAGGAA AATGATTGCC ACAAGGCAAG     1020

AGGATGCATC TTTCTTCCTG GTGTACAAGC CTTTAAAGAC TTCTGCTGCT GCTATGCCTC     1080

TTGGATGCAC ACTTTGTGTG TACATAGTTA CCTTTAACTC AGTGGTTATC TAATAGCTCT     1140

AAACTCATTA AAAAACTCC AAGCCTTCCA CCAAAACAGT GCCCCACCTG TATACATTTT      1200

TATTAAAAAA ATGTAATGCT TATGTATAAA CATGTATGTA ATATGCTTTC TATGAATGAT     1260

GTTTGATTTA AATATAATAC ATATTAAAAT GTATGGGAGA ACCAAAAAAA AAAAA          1315
```

(2) INFORMATION FOR SEQ ID NO:3:

(i) SEQUENCE CHARACTERISTICS:
        (A) LENGTH: 283 amino acids
        (B) TYPE: amino acid
        (C) STRANDEDNESS: single
        (D) TOPOLOGY: linear (vii) IMMEDIATE SOURCE:
        (A) LIBRARY: GENBANK
        (B) CLONE: 1487873

(xi) SEQUENCE DESCRIPTION: SEQ ID NO:3:

```
Met Phe Asp Lys Thr Arg Leu Pro Tyr Val Ala Leu Asp Val Ile Cys
  1               5                  10                  15

Val Leu Leu Ala Gly Leu Pro Phe Ala Ile Leu Thr Ser Arg His Thr
             20                  25                  30

Pro Phe Gln Arg Gly Ile Phe Cys Asn Asp Asp Ser Ile Lys Tyr Pro
         35                  40                  45

Tyr Lys Glu Asp Thr Ile Pro Tyr Ala Leu Leu Gly Gly Ile Val Ile
     50                  55                  60

Pro Phe Cys Ile Ile Val Met Ser Ile Gly Glu Ser Leu Ser Val Tyr
 65                  70                  75                  80

Phe Asn Val Leu His Ser Asn Ser Phe Val Gly Asn Pro Tyr Ile Ala
                 85                  90                  95

Thr Ile Tyr Lys Ala Val Gly Ala Phe Leu Phe Gly Val Ser Ala Ser
            100                 105                 110

Gln Ser Leu Thr Asp Ile Ala Lys Tyr Thr Ile Gly Ser Leu Arg Pro
        115                 120                 125

His Phe Leu Ala Ile Cys Asn Pro Asp Trp Ser Lys Ile Asn Cys Ser
    130                 135                 140

Asp Gly Tyr Ile Glu Asp Tyr Ile Cys Gln Gly Asn Glu Glu Lys Val
145                 150                 155                 160

Lys Glu Gly Arg Leu Ser Phe Tyr Ser Gly His Ser Ser Phe Ser Met
                165                 170                 175
```

-continued

```
Tyr Cys Met Leu Phe Val Ala Leu Tyr Leu Gln Ala Arg Met Lys Gly
            180                 185                 190

Asp Trp Ala Arg Leu Leu Arg Pro Met Leu Gln Phe Gly Leu Ile Ala
        195                 200                 205

Phe Ser Ile Tyr Val Gly Leu Ser Arg Val Ser Asp Tyr Lys His His
    210                 215                 220

Trp Ser Asp Val Thr Val Gly Leu Ile Gln Gly Ala Ala Met Ala Ile
225                 230                 235                 240

Leu Val Ala Leu Tyr Val Ser Asp Phe Phe Lys Asp Thr His Ser Tyr
                245                 250                 255

Lys Glu Arg Lys Glu Glu Asp Pro His Thr Thr Leu His Glu Thr Ala
            260                 265                 270

Ser Ser Arg Asn Tyr Ser Thr Asn His Glu Pro
        275                 280
```

(2) INFORMATION FOR SEQ ID NO:4:

(i) SEQUENCE CHARACTERISTICS:
        (A) LENGTH: 370 amino acids
        (B) TYPE: amino acid
        (C) STRANDEDNESS: single
        (D) TOPOLOGY: linear (vii) IMMEDIATE SOURCE:
        (A) LIBRARY: COLNNOT22
        (B) CLONE: 1734452

(xi) SEQUENCE DESCRIPTION: SEQ ID NO:4:

```
Met Ala Ala Glu Arg Gln Glu Ala Leu Arg Glu Phe Val Ala Val Thr
1               5                   10                  15

Gly Ala Glu Glu Asp Arg Ala Arg Phe Phe Leu Glu Ser Ala Gly Trp
            20                  25                  30

Asp Leu Gln Ile Ala Leu Ala Ser Phe Tyr Glu Asp Gly Gly Asp Glu
        35                  40                  45

Asp Ile Val Thr Ile Ser Gln Ala Thr Pro Ser Ser Val Ser Arg Gly
    50                  55                  60

Thr Ala Pro Ser Asp Asn Arg Val Thr Ser Phe Arg Asp Leu Ile His
65                  70                  75                  80

Asp Gln Asp Glu Asp Glu Glu Glu Glu Gly Gln Arg Phe Tyr Ala
                85                  90                  95

Gly Gly Ser Glu Arg Ser Gly Gln Gln Ile Val Gly Pro Pro Arg Lys
            100                 105                 110

Lys Ser Pro Asn Glu Leu Val Asp Asp Leu Phe Lys Gly Ala Lys Glu
        115                 120                 125

His Gly Ala Val Ala Val Glu Arg Val Thr Lys Ser Pro Gly Glu Thr
    130                 135                 140

Ser Lys Pro Arg Pro Phe Ala Gly Gly Gly Tyr Arg Leu Gly Ala Ala
145                 150                 155                 160

Pro Glu Glu Glu Ser Ala Tyr Val Ala Gly Glu Lys Arg Gln His Ser
                165                 170                 175

Ser Gln Asp Val His Val Val Leu Lys Leu Trp Lys Ser Gly Phe Ser
            180                 185                 190

Leu Asp Asn Gly Glu Leu Arg Ser Tyr Gln Asp Pro Ser Asn Ala Gln
        195                 200                 205

Phe Leu Glu Ser Ile Arg Arg Gly Glu Val Pro Ala Glu Leu Arg Arg
    210                 215                 220

Leu Ala His Gly Gly Gln Val Asn Leu Asp Met Glu Asp His Arg Asp
```

```
225                 230                 235                 240
Glu Asp Phe Val Lys Pro Lys Gly Ala Phe Lys Ala Phe Thr Gly Glu
                245                 250                 255
Gly Gln Lys Leu Gly Ser Thr Ala Pro Gln Val Leu Ser Thr Ser Ser
            260                 265                 270
Pro Ala Gln Gln Ala Glu Asn Glu Ala Lys Ala Ser Ser Ser Ile Leu
        275                 280                 285
Ile Asp Glu Ser Glu Pro Thr Thr Asn Ile Gln Ile Arg Leu Ala Asp
    290                 295                 300
Gly Gly Arg Leu Val Gln Lys Phe Asn His Ser His Arg Ile Ser Asp
305                 310                 315                 320
Ile Arg Leu Phe Ile Val Asp Ala Arg Pro Ala Met Ala Ala Thr Ser
                325                 330                 335
Phe Ile Leu Met Thr Thr Phe Pro Asn Lys Glu Leu Ala Asp Glu Ser
            340                 345                 350
Gln Thr Leu Lys Glu Ala Asn Leu Leu Asn Ala Val Ile Val Gln Arg
        355                 360                 365
Leu Thr
    370

(2) INFORMATION FOR SEQ ID NO:5:

(i) SEQUENCE CHARACTERISTICS:
        (A) LENGTH: 2707 base pairs
        (B) TYPE: nucleic acid
        (C) STRANDEDNESS: single
        (D) TOPOLOGY: linear (vii) IMMEDIATE SOURCE:
        (A) LIBRARY: COLNNOT22
        (B) CLONE: 1734452

(xi) SEQUENCE DESCRIPTION: SEQ ID NO:5:

AAGATGGCGG CGGAGCGACA GGAGGCGCTG AGGGAGTTCG TGGCGGTGAC GGGCGCCGAG      60
GAGGACCGGG CCCGCTTCTT TCTCGAGTCG GCCGGCTGGG ACTTGCAGAT CGCGCTAGCG     120
AGCTTTTATG AGGACGGAGG GGATGAAGAC ATTGTGACCA TTTCGCAGGC AACCCCCAGT     180
TCAGTGTCCA GAGGCACAGC CCCCAGTGAT AATAGAGTGA CATCCTTCAG AGACCTCATT     240
CATGACCAAG ATGAAGATGA GGAGGAAGAG GAAGGCCAGA GGTTTTATGC TGGGGGCTCA     300
GAGAGAAGTG GACAGCAGAT TGTTGGCCCT CCCAGGAAGA AAAGTCCCAA CGAGCTGGTG     360
GATGATCTCT TTAAAGGTGC CAAAGAGCAT GGAGCTGTAG CTGTGGAGCG AGTGACCAAG     420
AGCCCTGGAG AGACCAGTAA ACCGAGACCA TTTGCAGGAG GTGGCTACCG CCTTGGGGCA     480
GCACCAGAGG AAGAGTCTGC CTATGTGGCA GGAGAAAAGA GGCAGCATTC CAGCCAAGAT     540
GTTCATGTAG TATTGAAACT CTGGAAGAGT GGATTCAGCC TGGATAATGG AGAACTCAGA     600
AGCTACCAAG ACCCATCCAA TGCCCAGTTT CTGGAGTCTA TCCGCAGAGG GGAGGTGCCA     660
GCAGAGCTTC GGAGGCTAGC TCACGGTGGA CAGGTGAACT TGGATATGGA GGACCATCGG     720
GACGAGGACT TTGTGAAGCC CAAAGGAGCC TTCAAAGCCT TCACTGGCGA GGGTCAGAAA     780
CTGGGCAGCA CTGCCCCCCA GGTGTTGAGT ACCAGCTCTC CAGCCCAACA GGCAGAAAAT     840
GAAGCCAAAG CCAGCTCTTC CATCTTAATC GACGAATCAG AGCCTACCAC AAACATCCAA     900
ATTCGGCTTG CAGACGGCGG GAGGCTGGTG CAGAAATTTA ACCACAGCCA CAGGATCAGC     960
GACATCCGAC TCTTCATCGT GGATGCCCGG CCAGCCATGG CTGCCACCAG CTTTATCCTC    1020
ATGACTACTT TCCCGAACAA AGAGCTGGCT GATGAGAGCC AGACCCTGAA GGAAGCCAAC    1080
```

```
CTGCTCAATG CTGTCATCGT GCAGCGGTTA ACATAACCGC CCAGCCAGCT GCCTGGCCTC    1140

CCTCCTGTGT TTCCCATGGC CAGTGGCCAT GCCCCATGGG GATCGCCCCT CCTGCCCCCT    1200

TGTGCACACC CAGCAGTCCA GTGCAACGTC TCCTCCATAG CTCTGGGTTC TTAGATCTTG    1260

GTTGGACGTT TGTTTTCTCC TTAGTTGCAT TTCCTGGGTT TTTGTGATGA TCAATGGACT    1320

TTAATGAAAA AAAAAATAAA AACAACCAAA AAAATTGAAG GAATATCACC AGCATGTTGT    1380

ACGGAAACTC TCCCACTGAA GCAGGCTTTA ATTGCTTTAA AATTATATTT ATCTTGGGGC    1440

CTGTGGGAGG AATCTTCCTT CCATCTTCTC TGCATAAAAA CTTGTGGCAC ACAATGCTTA    1500

TTCACTAGTG TGTCCCACCC GCCAGCCCCA CAGATGACTG GAGGAAGGAG GGGAAATGTG    1560

TAGAAAGAGG CTTCGCCACC ACTTGTTCCC ACGAGAATAT ATCACTTGCC CAGATAAAAC    1620

TGGGCGGCAG CAGAGTTCCC TGAAGTGGGA AGTCAGAGCT CCATGCACAC AGTGTCTTCA    1680

GAAGGTGAAA ATAAATATTT CCCTGTGCTC CTTTTACTCA ACCCCTGGGG TATCTAATCT    1740

TGCCAGGTCT TGGCCAGTTG AGATTCTGTT CCACCTGCCT GCCTGGCCCT TTCCTCCATT    1800

ACCATCCAGA CTGCTCGCCT CCTGGGGATT CTCAGGGGCT CCATTATGGC TTGATTTACT    1860

CCACGTGCAG AAGTCTTGAG TGGACCTAGG AGGTAGGTGG GATATTTTTT TTCACTAGGA    1920

TACAGCTCAT GCCAACCCAT CCTAAGTGAG TTCAGAATCA GGGTATCTTG CCCTAAAAGA    1980

TAAACAGTCA AAATGCCACC GAGCTGTTCA CTAGTGATGT GTGGCAAATC AAATCAACTG    2040

TTGAAGAAGG GGTGAGTTTT CTGTGCTACA AGCACCTGTC ACTGTTGGTA CTTGCAGGAG    2100

GCTTCTGCTG GGTATGTTTT GGAAGTGAGT GTCACTACTT GGCTTTGCTT AGCAGGTTCT    2160

GCTTCACACT TGTTCTTTGA CCTGCTGACT TGTGACTTGC AGAAACATAG GCAGTAGTCC    2220

TAGCCTGGTA AAGACCCTCC ACCACCCCTA TAAGTTTGAT TGCTATGCAG GTTTGGGAGA    2280

GGAGGCCTAT TGGGCTCTTG GATGGAACCC TTTCCCGTAT TAAACAAACC AGAGACAGAA    2340

TCAGTGCTGA CTCAGGATCT CCTGGTTTGG AATCGTAATG TGCCTCAATC CTCTTTCCAA    2400

GCAGGCCTCA CCAGTCTCTT TCTCTTTCCT GCTTCACCCC TGCAATGAGC CAAGAACCAA    2460

CACTACATCC ACCTAGAACT GCAGAAGGGC TTGTGGTTTC AACCAAGACC CATCCTGAGC    2520

AAGGGACTTG GCTTGGTGCT TTTGATCCCA AAGTTCCCAC ACCGGCAGTG GCCTGCTGGG    2580

GCAATGGCAT CTGTCACGGT GTTTTCTCCA GCAGGTGGAG ATTATGGAAC CTACATATGG    2640

GTCTGGAAAA ACTGTACACT GTTGTCACCT TGACCATTAA AAACCAGAAT GAGGACAAAA    2700

AAAAAAA    2707
```

(2) INFORMATION FOR SEQ ID NO:6:

(i) SEQUENCE CHARACTERISTICS:
        (A) LENGTH: 370 amino acids
        (B) TYPE: amino acid
        (C) STRANDEDNESS: single
        (D) TOPOLOGY: linear (vii) IMMEDIATE SOURCE:
        (A) LIBRARY: GENBANK
        (B) CLONE: 2285790

(xi) SEQUENCE DESCRIPTION: SEQ ID NO:6:

```
Met Ala Glu Glu Arg Gln Asp Ala Leu Arg Glu Phe Val Ala Val Thr
 1               5                  10                  15

Gly Ala Glu Glu Asp Arg Ala Arg Phe Phe Leu Glu Ser Ala Gly Trp
            20                  25                  30

Asp Leu Gln Ile Ala Leu Ala Ser Phe Tyr Glu Asp Gly Gly Asp Glu
```

-continued

```
             35                  40                  45
Asp Ile Val Thr Ile Ser Gln Ala Thr Pro Ser Ser Val Ser Arg Gly
     50                  55                  60
Thr Ala Pro Ser Asp Asn Arg Val Thr Ser Phe Arg Asp Leu Ile His
 65                  70                  75                  80
Asp Gln Asp Glu Glu Glu Glu Glu Glu Gly Gln Arg Phe Tyr Ala
                 85                  90                  95
Gly Gly Ser Glu Arg Ser Gly Gln Gln Ile Val Gly Pro Pro Arg Lys
                100                 105                 110
Lys Ser Pro Asn Glu Leu Val Asp Asp Leu Phe Lys Gly Ala Lys Glu
            115                 120                 125
His Gly Ala Val Ala Val Glu Arg Val Thr Lys Ser Pro Gly Glu Thr
        130                 135                 140
Ser Lys Pro Arg Pro Phe Ala Gly Gly Gly Tyr Arg Leu Gly Ala Ala
145                 150                 155                 160
Pro Glu Glu Glu Ser Ala Tyr Val Ala Gly Glu Arg Arg Arg His Ser
                165                 170                 175
Gly Gln Asp Val His Val Val Leu Lys Leu Trp Lys Thr Gly Phe Ser
                180                 185                 190
Leu Asp Asn Gly Asp Leu Arg Ser Tyr Gln Asp Pro Ser Asn Ala Gln
            195                 200                 205
Phe Leu Glu Ser Ile Arg Arg Gly Glu Val Pro Ala Glu Leu Arg Arg
        210                 215                 220
Leu Ala His Gly Gly Gln Val Asn Leu Asp Met Glu Asp His Arg Asp
225                 230                 235                 240
Glu Asp Phe Val Lys Pro Lys Gly Ala Phe Lys Ala Phe Thr Gly Glu
                245                 250                 255
Gly Gln Lys Leu Gly Ser Thr Ala Pro Gln Val Leu Asn Thr Ser Ser
                260                 265                 270
Pro Ala Gln Gln Ala Glu Asn Glu Ala Lys Ala Ser Ser Ser Ile Leu
            275                 280                 285
Ile Asn Glu Ala Glu Pro Thr Thr Asn Ile Gln Ile Arg Leu Ala Asp
        290                 295                 300
Gly Gly Arg Leu Val Gln Lys Phe Asn His Ser His Arg Ile Ser Asp
305                 310                 315                 320
Ile Arg Leu Phe Ile Val Asp Ala Arg Pro Ala Met Ala Ala Thr Ser
                325                 330                 335
Phe Val Leu Met Thr Thr Phe Pro Asn Lys Glu Leu Ala Asp Glu Asn
                340                 345                 350
Gln Thr Leu Lys Glu Ala Asn Leu Leu Asn Ala Val Ile Val Gln Arg
            355                 360                 365
Leu Thr
    370
```